United States Patent
Ahn

(10) Patent No.: US 10,173,039 B2
(45) Date of Patent: Jan. 8, 2019

(54) BALLOON CATHETER

(71) Applicant: Yong Chul Ahn, Seongnam-si (KR)

(72) Inventor: Yong Chul Ahn, Seongnam-si (KR)

( * ) Notice: Subject to any disclaimer, the term of this patent is extended or adjusted under 35 U.S.C. 154(b) by 236 days.

(21) Appl. No.: 15/150,688

(22) Filed: May 10, 2016

(65) Prior Publication Data

US 2016/0250455 A1 Sep. 1, 2016

Related U.S. Application Data

(63) Continuation of application No. PCT/KR2014/010801, filed on Nov. 11, 2014.

(30) Foreign Application Priority Data

Nov. 11, 2013 (KR) .......... 10-2013-0136166
Nov. 11, 2013 (KR) .......... 10-2013-0136167

(51) Int. Cl.
| | | |
|---|---|---|
| *A61M 25/10* | (2013.01) | |
| *A61M 25/00* | (2006.01) | |
| *A61B 17/88* | (2006.01) | |
| *A61B 17/16* | (2006.01) | |

(52) U.S. Cl.
CPC .. *A61M 25/10184* (2013.11); *A61M 25/0082* (2013.01); *A61M 25/0097* (2013.01); *A61B 17/1617* (2013.01); *A61B 17/8855* (2013.01); *A61M 25/1006* (2013.01); *A61M 2025/1093* (2013.01)

(58) Field of Classification Search
CPC ........ A61M 25/10184; A61M 25/1006; A61M 25/0082; A61M 2025/1093; A61M 2025/1063; A61M 25/10; A61M 25/0097; A61B 17/1617; A61B 17/8855
See application file for complete search history.

(56) References Cited

U.S. PATENT DOCUMENTS

| | | | |
|---|---|---|---|
| 4,395,806 A | | 8/1983 | Wonder et al. |
| 5,454,788 A | * | 10/1995 | Walker .................. A61L 29/04 604/103 |
| 6,837,871 B2 | | 1/2005 | Gonzales et al. |
| 9,199,058 B2 | | 12/2015 | Lentz |

(Continued)

FOREIGN PATENT DOCUMENTS

| | | |
|---|---|---|
| JP | 2001-500023 A | 1/2001 |
| JP | 2002-360702 A | 12/2002 |

(Continued)

OTHER PUBLICATIONS

Japanese Office Action (JP 2016-553196), JPO, dated Mar. 7, 2017.

(Continued)

*Primary Examiner* — Katrina Stransky
(74) *Attorney, Agent, or Firm* — Park & Associates IP Law, P.C.

(57) ABSTRACT

The present invention provides a balloon catheter comprising: an elastic catheter tube in which a second tube is slidably inserted into a first tube; and an elasticity restriction means for restricting the elasticity of the catheter tube with an elasticity rate thereof by connecting the first tube and the second tube, or a balloon catheter in which an inflation lumen and a guide wire lumen of a catheter tube are integrated.

5 Claims, 14 Drawing Sheets

(56) References Cited

U.S. PATENT DOCUMENTS 9,352,133 B2    5/2016   Godin et al.
2009/0177235 A1  7/2009   Saab et al.

FOREIGN PATENT DOCUMENTS

| | | |
|---|---|---|
| JP | 2006-521877 A | 9/2006 |
| JP | 2008-543368 A | 12/2008 |
| JP | 2011-67660 | 4/2011 |
| JP | 2013-516209 A | 5/2013 |
| KR | 10-2009-0005283 A | 1/2009 |
| KR | 10-2013-0104897 A | 9/2013 |
| WO | 97-28840 A1 | 8/1997 |
| WO | 97-37714 A1 | 10/1997 |
| WO | 2011-080778 A1 | 7/2011 |

OTHER PUBLICATIONS

International Search Report(PCT/KR2014/010801), WIPO, dated Mar. 18, 2015.
Korean Office Action(KR 10-2013-0136166), KIPO, dated Mar. 23, 2015.
Korean Office Action(KR 10-2013-0136167), KIPO, dated Mar. 23, 2015.

\* cited by examiner

BALLOON CATHETER

REFERENCE TO RELATED APPLICATIONS

This is a continuation of pending International Patent Application PCT/KR2014/010801 filed on Nov. 11, 2014, which designates the United States and claims priority of Korean Patent Applications No. 10-2013-0136166 and 10-2013-0136167 both filed on Nov. 11, 2013, the entire contents of which are incorporated herein by reference.

FIELD OF THE INVENTION

The present invention generally relates to a medical balloon catheter.

BACKGROUND OF THE INVENTION

In general, a balloon catheter applicable for medical uses includes a catheter tube having a lumen extending in the longitudinal direction between opposite ends thereof, a balloon connected to one end of the catheter tube, and a connector connected to the other end of the catheter tube. A fluid injector, such as a syringe, is connected to the connector. The balloon catheter like this is configured such that fluid (possibly liquid) injected into the lumen of the catheter tube from the fluid injector is delivered through the lumen and the balloon is inflated by fluid that has passed through the lumen.

The balloon catheter is inserted into an inner portion (bone, an internal organ, a blood vessel, or the like) of the body from the skin of a subject through a previously-formed surgical passage, with the balloon being contracted (in its original shape). When the balloon catheter is inserted into the portion to be operated on, the balloon is inflated by fluid supplied from the fluid injector to expand the corresponding tissues or restore damaged tissues in the body to an original state.

An amount by which the balloon is inflated and the inflated shape of the balloon is mainly determined by the pressure of fluid applied to the balloon. Thus, when the pressure of fluid applied to the balloon is inaccurately controlled such that an excessive amount of pressure is applied to the balloon, the balloon may be inflated beyond a required level, thereby being deformed to an abnormal shape different from a required shape. For example, the abnormal shape of the balloon may be a shape where one portion is more inflated than the other portions. A variety of abnormal shapes may be caused by coupling relationships with the catheter tube. An abnormally-inflated shape balloon may lead to treatment difficulty and may significantly lower the accuracy of the surgical treatment.

After the balloon catheter is inserted into the body through the surgical passage, when the balloon catheter cannot reach the intended position, the inserted balloon catheter must be removed from the portion to be operated and the surgical passage must be extended. Thereafter, the balloon catheter is reinserted into the body. However, this process is very complicated and is disadvantageous in terms of the speed of the surgical treatment, the improvement of which is required.

In addition, the lumen of the catheter tube includes an inflating lumen, through which fluid from the fluid injector is delivered, and a guide wire lumen, through which a guide wire reinforcing the strength of the catheter tube is inserted. Since the inflating lumen and the guide wire lumen are separately provided on the catheter tube in this manner, it is difficult to fabricate the balloon catheter. In addition, the balloon catheter has a complicated structure, and the outer diameter of the catheter tube has to be increased.

SUMMARY OF THE INVENTION

The present invention is intended to propose a balloon catheter that is advantages in terms of the reliability of surgical treatment and operator convenience.

Also intended is proposal of a balloon catheter that has a simple structure and is advantageous in terms of surgical treatment.

In order to achieve the above object, according to one aspect of the present invention, a balloon catheter may include: an extensible and compressible catheter tube including a first tube having a first lumen and a second tube having a second lumen communicating with the first lumen, a through-hole being formed on the outer circumference of the second tube, a proximal end portion of the second tube being slidably inserted into the first tube through a distal end portion of the first tube; a balloon fitted around the outer circumference of the catheter tube, opposite ends of the balloon being coupled to the outer circumference of the distal end portion of the first tube and the outer circumference of a distal end portion of the second tube. The balloon is inflated by fluid discharged through the through-hole; and an extension/compression restricting means having a predetermined degree of resilience, the extension/compression restricting means connecting the first tube and the second tube to limit extension and contraction of the catheter tube due to the degree of resilience thereof.

The extension/compression restricting means may include a resilient member having opposite ends thereof coupled to the first tube and the second tube. Specifically, the opposite ends of the resilient member may be connected to the outer circumference of the first tube and the outer circumference of the second tube between the catheter tube and the balloon.

The resilient member may have a tubular structure. In addition, the resilient member may be a mesh.

The balloon catheter may further include a drill bit coupled to the distal end portion of the second tube in the longitudinal direction of the second tube.

The drill bit may include a shank fitted into the second tube through the distal end portion of the second tube and a bit body connected to the shank.

An inward projection may be provided on the inner circumference of the distal end portion of the first tube to butt against the proximal end portion of the second tube, thereby restricting the length of the catheter tube to be contracted. Alternatively, an inward projection may be provided on the inner circumference of the distal end portion of the first tube, and an outward projection may be provided on the outer circumference of the proximal end portion of the second tube to butt against the inward projection in order to prevent the first tube and the second tube from being separated from each other.

According to another aspect of the present invention, a balloon catheter may include: a catheter tube having a proximal end portion, a distal end portion, and a lumen between the proximal end portion and the distal end portion, with a through-hole being formed on the outer circumference of the distal end portion thereof; a balloon disposed on the outer circumference of the distal end portion of the catheter tube to be inflatable by fluid discharged through the through-hole; and a drill bit coupled to the distal end portion of the catheter tube in the longitudinal direction of the catheter tube.

According to further another aspect of the present invention, a balloon catheter may include: an extensible and compressible catheter tube including a first tube having a first lumen and a second tube having a second lumen communicating with the first lumen, a through-hole being formed on the outer circumference of the second tube, a proximal end portion of the second tube being slidably inserted into the first tube through a distal end portion of the first tube; and a balloon fitted around the outer circumference of the catheter tube, opposite ends of the balloon being coupled to the outer circumference of the distal end portion of the first tube and the outer circumference of a distal end portion of the second tube, wherein the balloon is inflated by fluid discharged through the through-hole. First and second inward projections are provided on the inner circumference of the distal end portion of the first tube, and an outward projection is provided on the outer circumference of the proximal end portion of the second tube between the first inward projection and the second inward projection to butt against the first inward projection or the second inward projection due to extension or contraction of the catheter tube.

According to another aspect of the present invention, a balloon catheter may include: a catheter tube including a proximal end portion, a distal end portion, and a single lumen extending between the proximal end portion and the distal end portion in the longitudinal direction; a guide wire extending through the catheter tube to be disposed on the lumen; a connector having a fluid injection passage extending therethrough in the longitudinal direction, the connector being coupled to the proximal end portion of the catheter tube such that the fluid injection passage communicates with the lumen, the connector including a guide wire holder, the guide wire holder including a holder body supporting a proximal end portion of the guide wire in a central portion of the fluid injection passage and at least one support arm supporting the holder body on an inner wall of the fluid injection passage; and a balloon disposed on the distal end portion of the catheter tube to be inflatable by fluid injected into the lumen from the fluid injection passage.

The guide wire may pass through the catheter tube, such that a distal end portion of the guide wire protrudes from the catheter tube. A reinforcement member may be coupled to the distal end portion of the guide wire. The balloon may be coupled to the catheter tube and the reinforcement member, with one end thereof being fitted around the outer circumference of the distal end portion of the catheter tube, and the other end thereof surrounding the reinforcing member.

A plurality of the support arms may be disposed around the holder body and may be spaced apart from each other. The connector may include a knob provided on the outer circumference thereof.

The connector may include: a first connector body coupled to the proximal end portion of the catheter tube, the first connector body having a first passage communicating with the lumen to form a portion of the fluid injection passage; and a second connector body coupled to the first connector body, the second connector body having a second passage communicating with the first passage to form the fluid injection passage together with the first passage, the guide wire holder being provided on the second passage.

The first connector body may include: a first engagement recess on one end, into which the proximal end portion of the catheter tube is fitted; and a second engagement recess on the other end, allowing for fitting engagement with the second connector body. The first passage of the first connector body may extend in the longitudinal direction between the first engagement recess and the second engagement recess. The second connector body may include a fitting portion fitted into the second engagement recess.

The guide wire holder may be disposed on a distal end portion of the second passage.

The foregoing technical solutions of the present invention will be specific and clear from exemplary embodiments (detailed features based on which the invention can be put into practice) to be described hereinafter and the accompanying drawings. In addition, a variety of other technical solutions in addition to the forgoing technical solutions will be proposed hereinafter.

According to embodiments of the present invention, the balloon catheter allows surgical treatment to be performed reliably and conveniently and can be easily fabricated at a low cost.

BRIEF DESCRIPTION OF THE DRAWINGS

FIGS. 2 and 3 are cross-sectional views of part A in FIG. 1, in which FIG. 2 illustrates a position in which the balloon is contracted, and FIG. 3 illustrates a position in which the balloon is inflated;

FIGS. 9 and 10 are cross-sectional views illustrating the balloon catheter according to the second embodiment of the present invention, in which FIG. 9 illustrates a position in which the balloon is contracted, and FIG. 10 illustrates a position in which the balloon is inflated;

DETAILED DESCRIPTION OF THE INVENTION

Reference will now be made in detail to exemplary embodiments of the present invention, examples of which are illustrated in the accompanying drawings. For reference, the dimensions of components illustrated on the drawings as well as the thicknesses of the lines thereof may be rather exaggerated for the sake of explanation. In addition, all terms used herein may be understood differently depending on the users, the intention of the users, practices, and the like, since they are defined considering the functions thereof in the present invention. Thus, these terms shall be defined to be consistent with their meaning in the context of the specification.

A balloon catheter according to an exemplary embodiment of the present invention may be inserted into bone, an internal organ, a blood vessel, or the like through a surgical passage that is previously formed to reach an intended position in the interior of the body from the skin of a subject.

In the description of embodiments of the present invention, the terms "proximal end portion" and "distal end portion" are defined with respect to the subject such that the end portion positioned adjacent to the subject is referred to as the proximal end portion, and the opposite end portion is referred to as the distal end portion.

Figure 1:
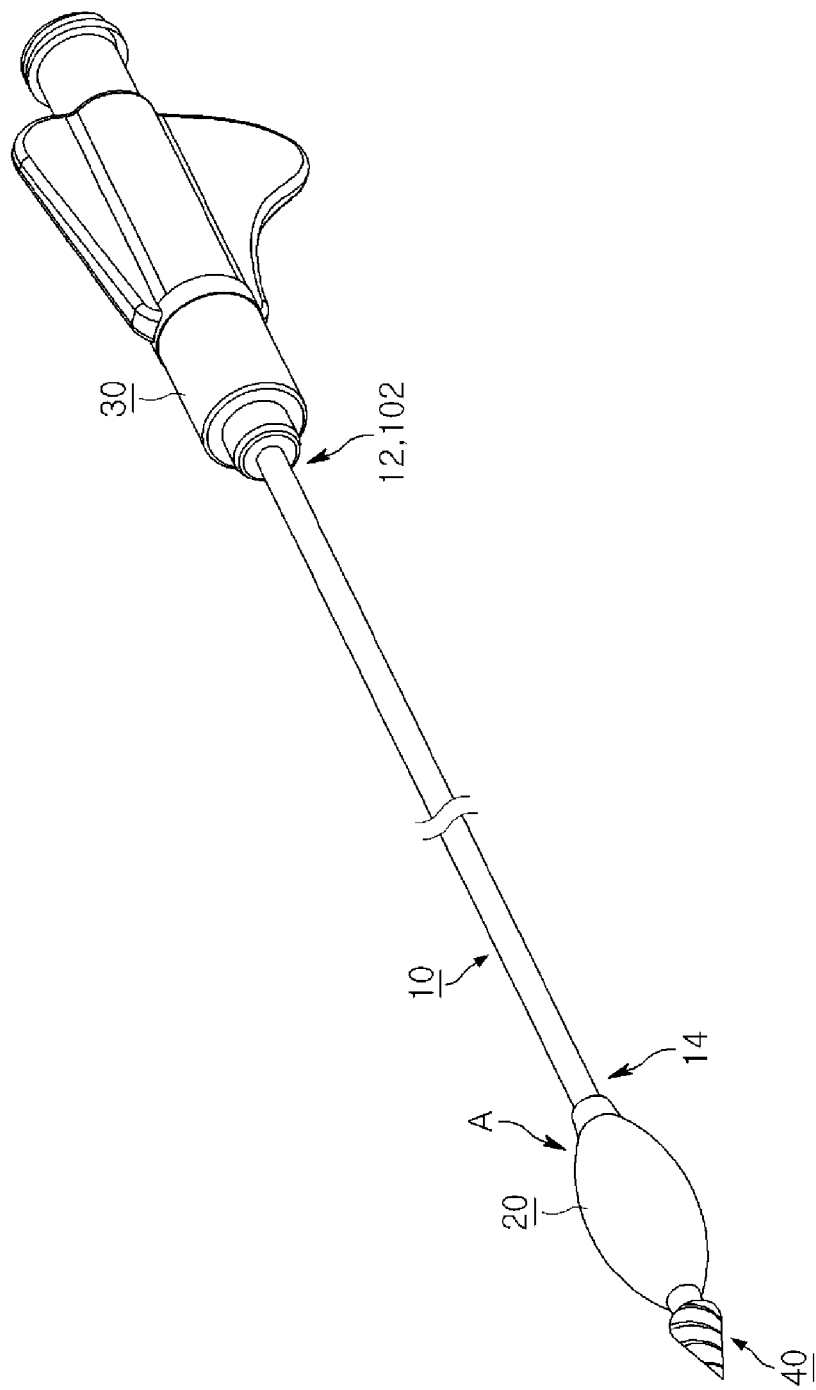
FIG. 1 is a perspective view illustrating a balloon catheter according to a first embodiment of the present invention.
Figure 2:
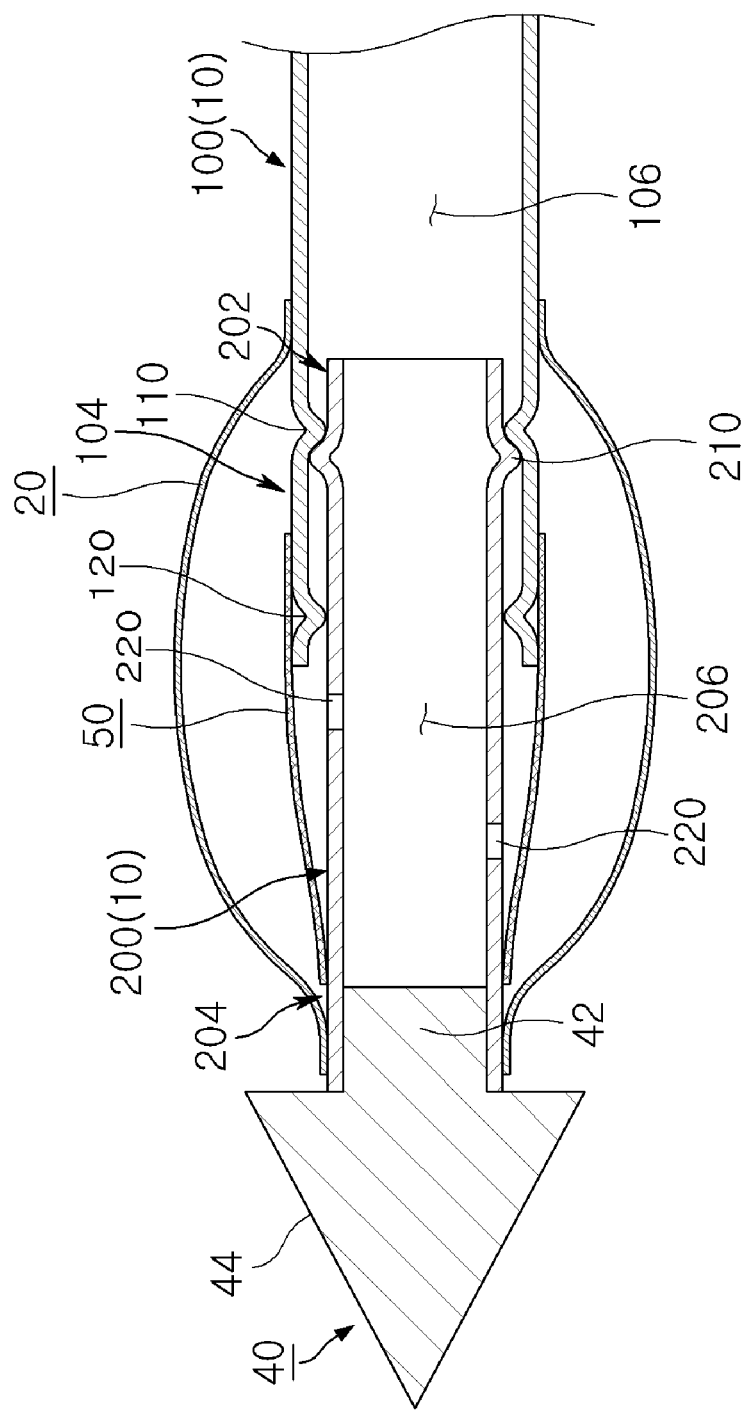
Figure 3:
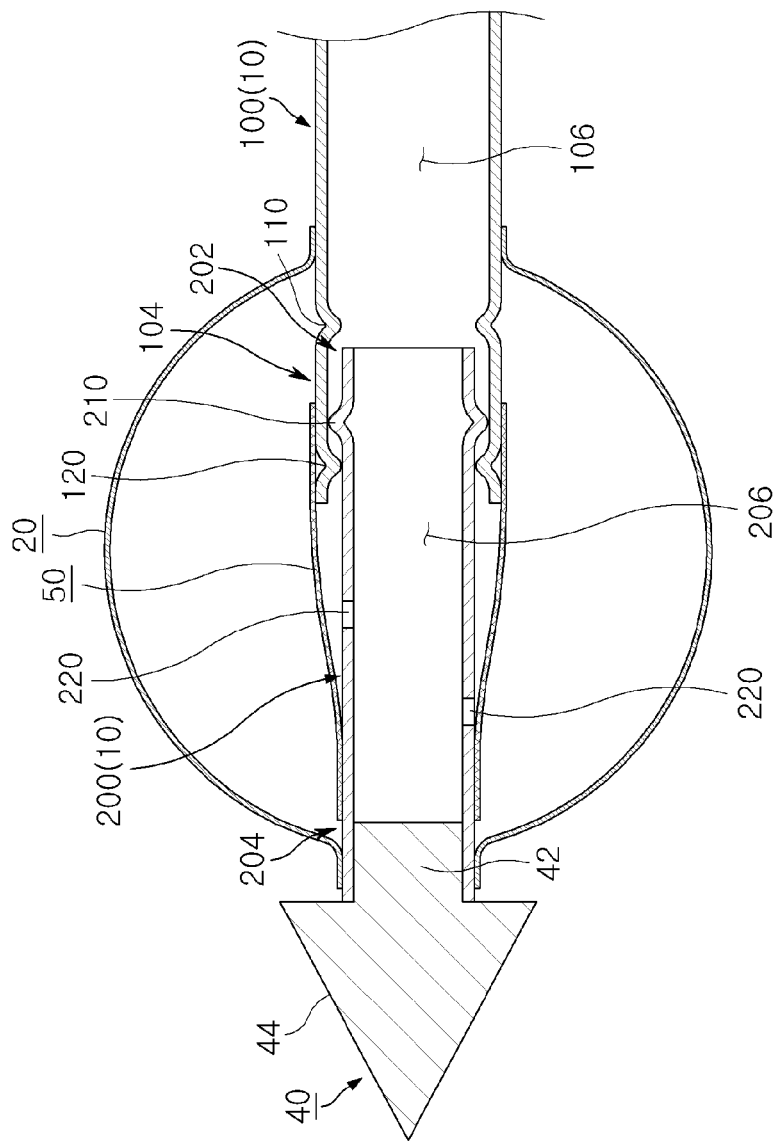
Figure 4:
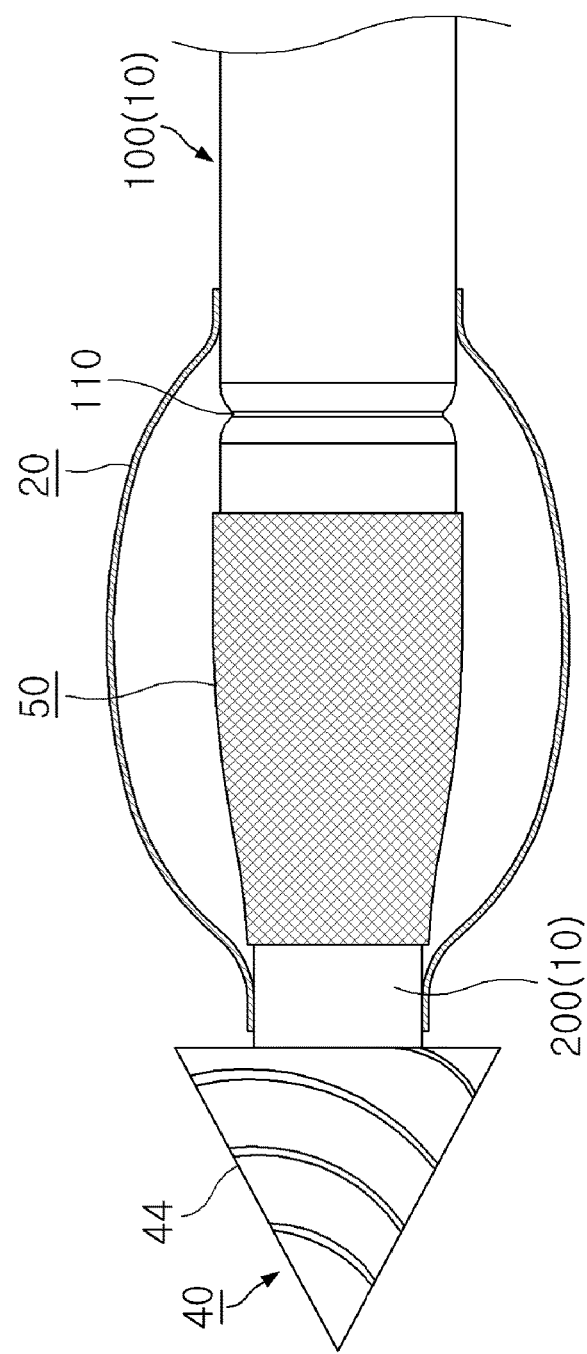
FIG. 4 is a partial cross-sectional view illustrating part A in FIG. 1.

FIGS. 1 to 4 illustrate a balloon catheter according to a first embodiment of the present invention. As illustrated in FIG. 1, the balloon catheter according to the first embodiment of the present invention includes a catheter tube 10 having a proximal end portion 12, distal end portion 14, and a lumen (refer to reference numbers 106 and 206 in FIGS. 2 and 3). The catheter tube 10 is extensible and compressible in the longitudinal direction. The balloon catheter also includes a balloon 20 disposed around the distal end portion 14 of the catheter tube 10, a connector 30 coupled to the proximal end portion 12 of the catheter tube 10, and a drill bit 40 coupled to the distal end of the catheter tube 10. The balloon catheter according to the first embodiment of the present invention will be described in detail by further referring to FIGS. 2 to 4.

The catheter tube 10 includes a first tube 100 and a second tube 200 telescopically coupled to each other.

The length of the first tube 10 is defined to make up the majority of the length of the catheter tube 10. The first tube 100 has a first end portion (see reference numeral 102 in FIG. 1) formed as a proximal end portion, a second end portion 104 formed as a distal end portion, and an inner first lumen 106 extending in the longitudinal direction of the first tube 100 between the first end portion 102 and the second end portion 104 of the first tube 100. The first end portion 102 of the first tube 100 forms the proximal end portion 12 of the catheter tube 10. The first tube 100 is configured such that opposite ends thereof are open, causing the first end portion 102 and the second end portion 104 of the first tube 100 to be open.

The second tube 200 is formed to have a relatively short length. That is, the length of the second tube 200 is shorter than the length of the first tube 100. The second tube 200 has a first end portion 202 formed as a proximal end portion, a second end portion 204 formed as a distal end portion, and an inner lumen 206 extending in the longitudinal direction of the second tube 200 between the first end portion 202 and the second end portion 204 of the second tube 200. The second end portion 204 of the second tube 200 forms the distal end portion 14 of the catheter tube 10. The second tube 200 is configured such that opposite ends thereof are open, causing the first end portion 202 and the second end portion 204 of the second tube 200 to be open The first end portion 202 of the second tube 200 is slide-movably inserted into the first tube 100 through the opening of the second end portion 104 of the first tube 100, such that the length of the catheter tube 10 is extensible and contractible in response to the relative movement of the first tube 100 and the second tube 200. In the first tube 100 and the second tube 200 coupled in this manner, the first lumen 106 and the second lumen 206 communicate with each other through the opening of the first end portion of the second tube 200. The first lumen 106 and the second lumen 206 communicating with each other form the lumen of the catheter tube 10.

A first inward projection 110 and a second inward projection 120 are provided on the inner circumference of the second end portion 104 of the first tube 100. The first inward projection 110 and the second inward projection 120 annularly extend along the inner circumference of the first tube 100. The first inward projection 110 and the second inward projection 120 are arranged at a predetermined distance from each other and are spaced apart from each other in the longitudinal direction. The second inward projection 120 is adjacent to the second end portion 104 of the first tube 100, while the first inward projection 110 is spaced apart from the second inward projection 120 in the direction of the first end portion 102 of the first tube 100.

An outward projection 210 is formed on the outer circumference of the first end portion 202 of the second tube 200 to butt against the first inward projection 110 or the second inward projection 120 in the area between the first inward projection 110 and the second inward projection 120 in response to the relative movement of the first tube 100 and the second tube 200. The outward projection 210 may be annularly formed on the outer circumference of the second tube 200. The outward projection 210 butts against the first inward projection 110 to restrict the length of the catheter tube 10 to be contracted when the length of the catheter tube 10 decreases in response to the relative movement of the first tube 100 and the second tube 200 and butts against the second inward projection 120 to restrict the length of the catheter tube 10 to be extended when the length of the catheter tube 10 increases in response to the relative movement of the first tube 100 and the second tube 200, thereby preventing the first tube 100 and the second tube 200 from being separated from each other.

One or more through-holes 220 communicating with the second lumen 206 are formed on the outer circumference between the first end portion 202 and the second end portion 204 of the second tube 200.

The first tube 100 may be formed of a metal having a relatively high level of strength. For example, the first tube 100 may be formed of stainless steel. When the strength of the catheter tube 10 is reinforced by forming the first tube 100 from a relatively strong metal, such as stainless steel, the catheter tube 10 can be prevented from being excessively bent when the balloon catheter according to the first embodiment of the present invention is inserted into the body of the subject. Although a conventional balloon catheter has two lumens in the catheter tube to reinforce the strength of the catheter tube, with a guide wire being inserted into one of the two lumens, the balloon catheter according to the first embodiment of the present invention has the first tube 100 formed of a relatively strong metal, the guide wire can be omitted.

The first tube 100 may be formed of a shape memory alloy such that the first tube 100 can return to the original shape from a deformed shape, such as a bent shape, when force applied to the catheter tube 10 is removed. The shape memory alloy may be implemented as nitinol, a nonmagnetic alloy of nickel (Ni) and titanium (Ti). The material of the first tube 100 is not limited to the above-stated metal, and a variety of materials able to reinforce the strength of the catheter tube 10 may be applied. Specifically, the first tube 100 may be formed of a synthetic resin, such as polymer. Alternatively, the first tube 100 may be configured such that the second end portion 104 of the first tube 100 is formed of a synthetic resin and the other portions except for the second end portion 104 of the first tube 100 are formed of a metal (e.g. a configuration including a synthetic resin tube and a metal tube coupled to each other).

The second tube 200, which is shorter than the first tube 100, may be formed of a synthetic resin (e.g. polymer). The second tube 200 may be formed of a metal according to operating conditions, or the like.

The balloon 20 is formed of a synthetic resin that is extensible and compressible (shape recoverable), and has a tubular structure. In the position in which the balloon 20 is fitted around the catheter tube 10, opposite ends of the balloon 20 are coupled to the outer circumference of the second end portion 104 of the first tube 100 and the outer circumference of the second end portion 204 of the second tube 200, such that the through-holes 220 positioned between the first end portion 202 and the second end portion 204 communicate with the interior of the balloon 20. The balloon 20 is coupled to the outer circumference of the second end portion 104 of the first tube 100 and the outer circumference of the second end portion 204 of the second tube 200 such that airtightness can be maintained. For example, opposite ends of the balloon 20 may be attached to the outer circumference of the second end portion 104 of the first tube 100 and the outer circumference of the second end portion 204 of the second tube 200 by means of an adhesive or the like or may be fixed thereto through close contact by means of a band or the like.

A fluid injector, such as a syringe, is connected to the connector 30. The connector 30 has a fluid passage through which fluid enters from the fluid injector, the fluid passage communicating with the opening of the first end portion 102 of the first tube 100.

The drill bit 40 is arranged along the longitudinal direction of the catheter tube 10. The drill bit 40 includes a shank 42 and a bit body 44 connected to the shank 42.

The shank 42 is fitted into the second tube 200 through the opening of the second end portion 204 of the second tube 200. The size of the shank 42 is set such that the shank 42 is in close contact with the inner circumference of the second end portion 204 of the second tube 200, so the shank 42 functions as a sealing means for sealing the opening of the second end portion 204 of the second tube 200. Although not shown, the outer circumference of the shank 42 may be coated with a sealing material in order to improve the sealing ability.

The bit body 44 may be formed integrally with the shank 42. Cutting blades are formed on the outer circumference of the bit body 44. It is preferable that the outermost circumference of the bit body 44 is similar to or slightly greater than that of the catheter tube 10.

Fluid (possibly liquid) from the fluid injector is injected into the lumen (see reference numerals 106 and 206) of the catheter tube 10, is delivered from the proximal end portion 12 toward the distal end portion 14 of the catheter tube 10 through the lumen of the catheter tube 10, and is discharged through the through-holes 220 to enter the balloon 20. The balloon 20 is inflated due to the action of fluid provided as described above, and the length of the catheter tube 10 increases through the relative movement of the first tube 100 and the second tube 200 depending on the amount of the inflation of the balloon 20 (see FIG. 3). Consequently, in the balloon catheter according to the first embodiment of the present invention, even if fluid having an excessive amount of pressure is applied to the balloon 20, the length of the catheter tube 10 can be increased through the relative movement of the first tube 100 and the second tube 200, thereby preventing the balloon 20 from being deformed to an abnormal shape different from the intended shape.

In the position in which the balloon 20 is inflated, when a force is applied to the catheter tube 10 in the longitudinal direction of the catheter tube 10, the length of the catheter tube 10 is decreased through the relative movement of the first tube 100 and the second tube 200, such that the shape of the balloon 20 may be changed. In order to prevent this, the balloon catheter according to the first embodiment of the present invention further includes an extension/compression restricting means (see reference numeral 50) for restricting the extension and compression of the catheter tube 10 by connecting the first tube 100 and the second tube 200.

The extension/compression restricting means includes a resilient member 50 having a predetermined degree of resilience (possibly modulus of elasticity). The resilient member 50 is disposed between the catheter tube 10 and the balloon 20, with opposite ends thereof being coupled to the outer circumference of the first tube 100 and the outer circumference of the second tube 200. The resilient member 50 allows the catheter tube 10 to maintain its length when force applied to the catheter tube 10 is not sufficient to extend or compress the resilient member 50 (the level is determined depending on the degree of resilience of the resilient member). In contrast, when relatively greater force is applied to the catheter tube 10, the catheter tube 10 is extended or contracted in length. The degree of resilience of the resilient member 50 is set such that the catheter tube 10 can extend in length when the balloon 20 is inflated. It is preferable that the resilient member 50 is in a compressed position, with opposite ends thereof being coupled to the outer circumference of the first tube 100 and the outer circumference of the second tube 200, when the balloon 20 is contracted.

The resilient member 50 as described above has a tubular structure that can be fitted around the catheter tube 10, and is implemented as a mesh. It is preferable that the resilient member 50 is implemented as a metal mesh. Fluid discharged through the through-holes 220 can be supplied to the balloon 20 through the holes of the mesh. The degree of resilience of the resilient member 50 may be set to a level as required by adjusting the thickness of wires (metal wires) of the mesh, the aperture ratio (number of holes) of the mesh, or the like.

Opposite ends of the resilient member 50 may be firmly attached to the outer circumference of the first tube 100 and the outer circumference of the second tube 200 by means of an adhesive or the like or may be fastened thereto by means of a fastener or the like.

Figure 5:
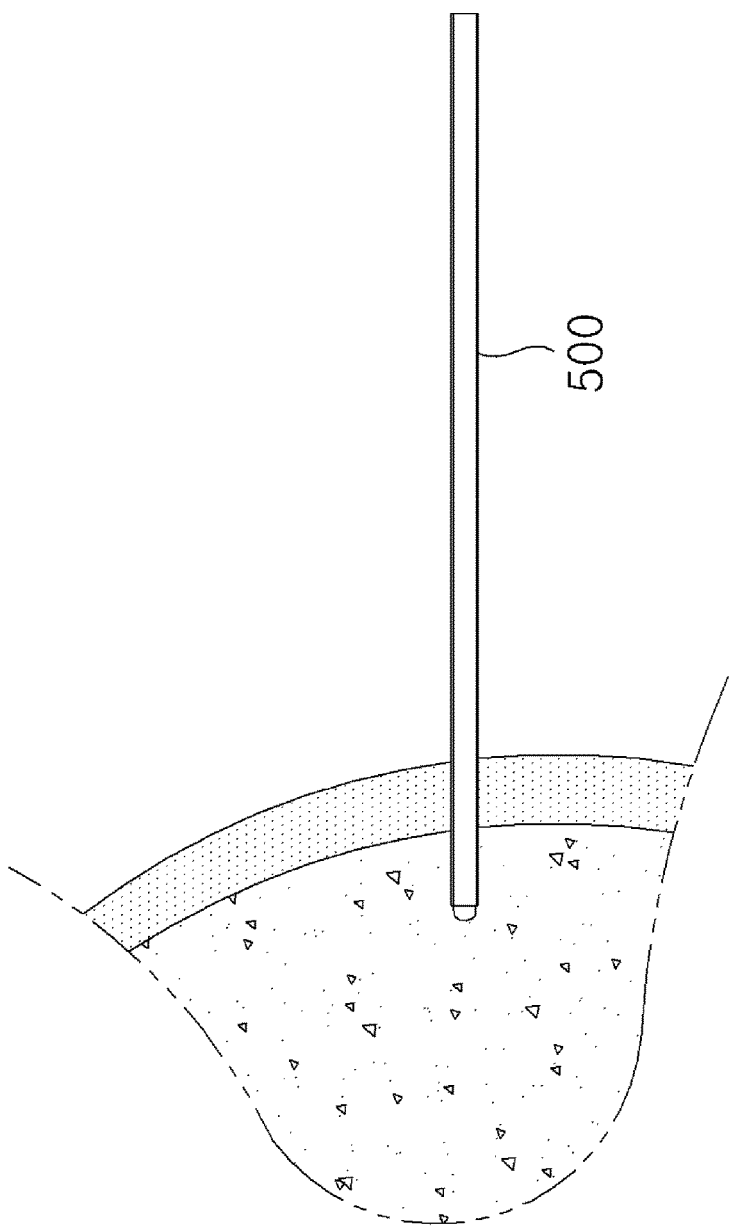
FIGS. 5 to 7 illustrate a bone surgery using the balloon catheter according to the first embodiment of the present invention.
Figure 6:
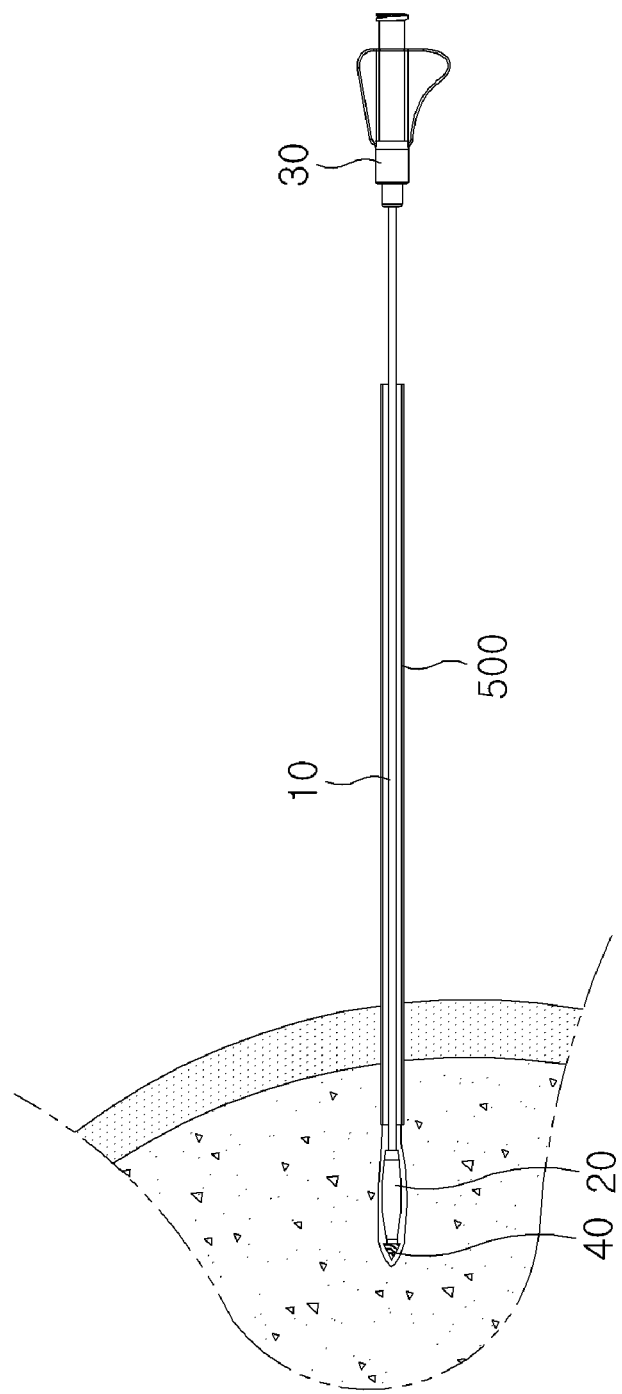
Figure 7:
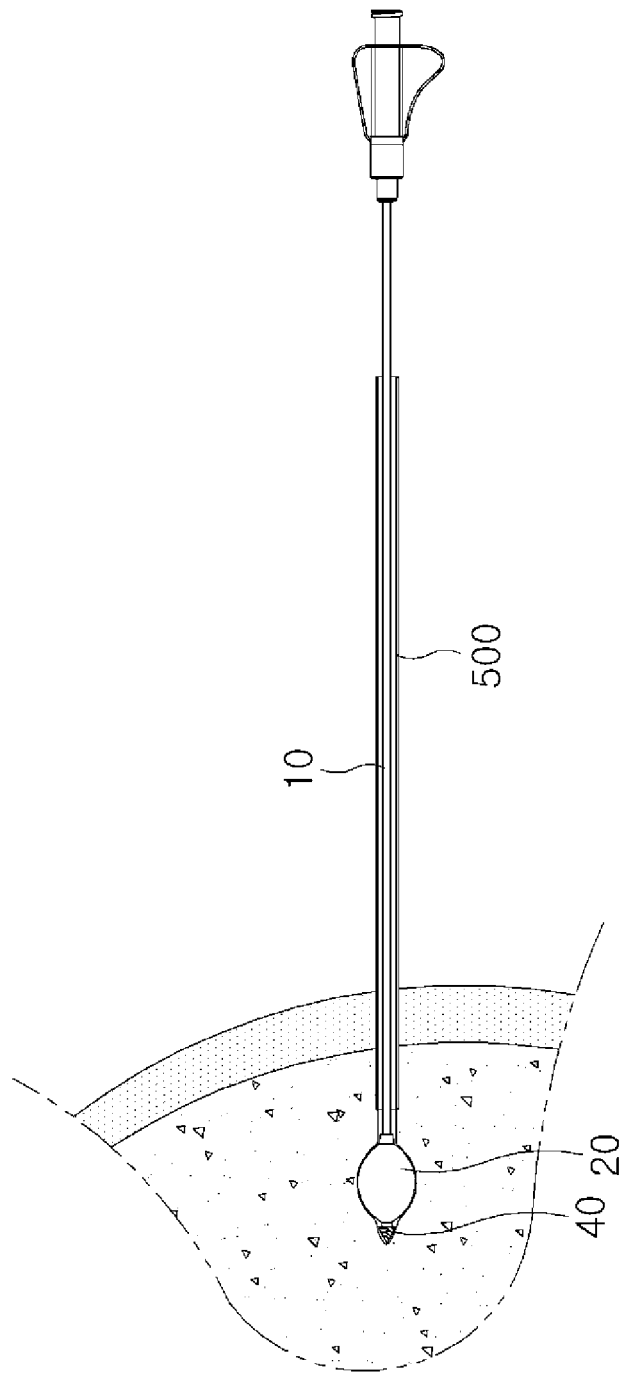

FIGS. 5 to 7 illustrate a bone surgery using the balloon catheter according to the first embodiment of the present invention. The balloon catheter according to the first embodiment of the present invention provides the following advantages when used in a surgery for relatively strong tissues, such as bone (possibly spinal bone).

The balloon catheter according to the first embodiment of the present invention is inserted into bone within the body from the skin of the subject through a surgical passage that has been previously formed using a needle instrument or a cannula instrument (see reference numeral 500 in FIGS. 5 to 7). The balloon catheter according to the first embodiment of the present invention is inserted in a state in which the balloon 20 is contracted.

After the balloon catheter according to the first embodiment of the present invention is inserted into the body of the subject, when the balloon catheter according to the first embodiment of the present invention cannot reach the intended position (when the surgical passage is not formed to a required depth), the drill bit 40 disposed on the distal end portion 14 of the catheter tube 10 is used to bring the balloon catheter according to the first embodiment of the present invention to the intended position (see FIG. 6). At this time, an operator (a surgeon) can extend the surgical passage by pushing, twisting, or hammering the balloon catheter according to the first embodiment of the present invention.

Since the surgical passage can be extended using the drill bit 40, it is possible to remove several problematic surgical procedures of removing the inserted balloon catheter from the body portion under the surgery, drilling the surgical passage using a needle instrument or the like in order to extend the surgical passage, and reinserting the balloon catheter.

When the balloon catheter according to the first embodiment of the present invention reaches the intended position within the body, the balloon 20 is inflated by injecting fluid thereinto, thereby expanding the corresponding tissues or restoring damaged tissues to an original state (see FIG. 7). Here, the catheter tube 10 extends in length through the relative movement of the first tube 100 and the second tube 200 in response to the inflation of the balloon 20. Due to the lengthwise extension of the catheter tube 10, the balloon 20 can be inflated ordinarily without being deformed to an abnormal shape. In addition, since the extension of the catheter tube 10 is limited by the resiliency of the resilient member 50, the resilient member 50 reliably maintains the inflated shape even if force is applied to the catheter tube 10.

FIGS. 8 to 14 illustrate a balloon catheter according to an exemplary embodiment of the present invention.

Figure 8:
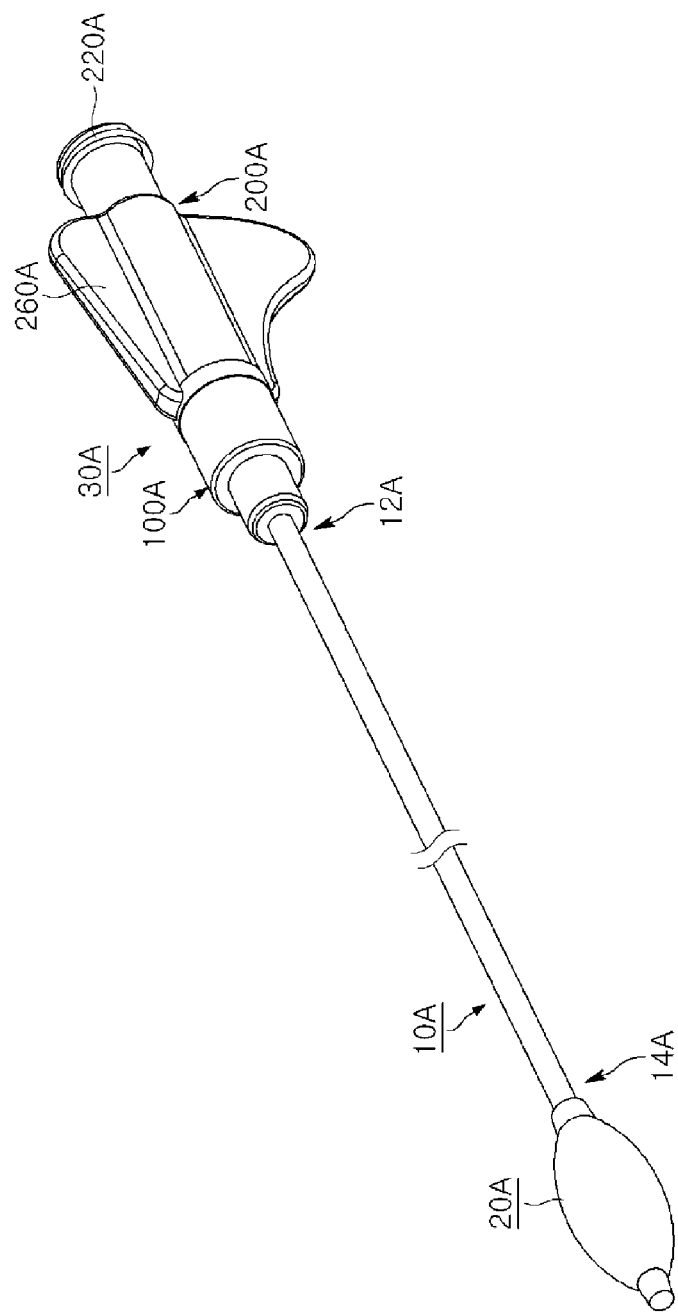
FIG. 8 is a perspective view illustrating a balloon catheter according to a second embodiment of the present invention.
Figure 9:
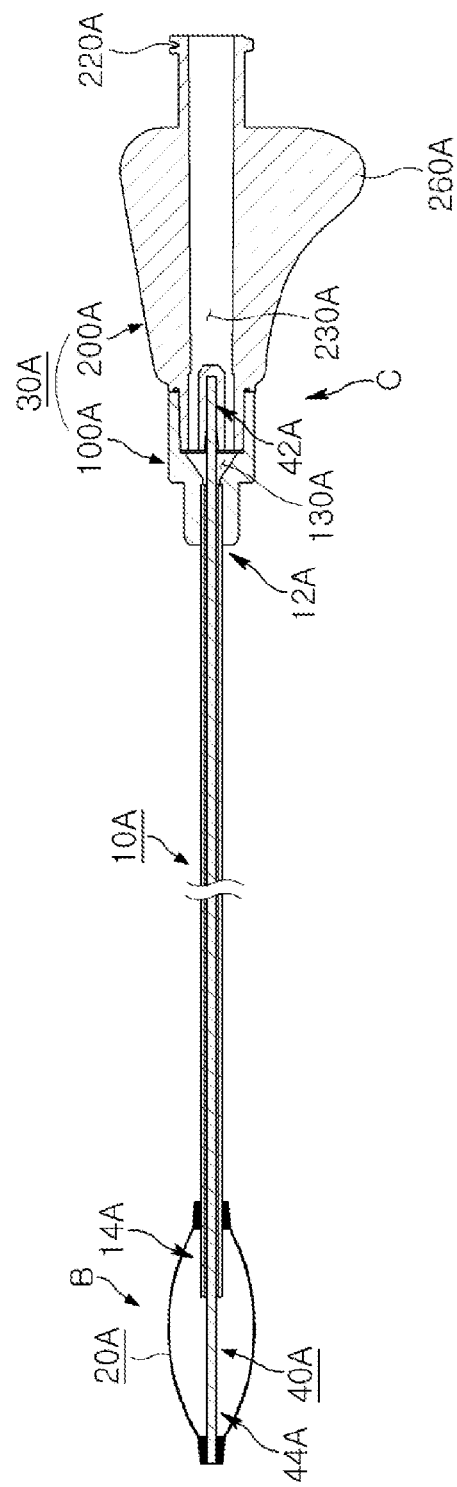
Figure 10:
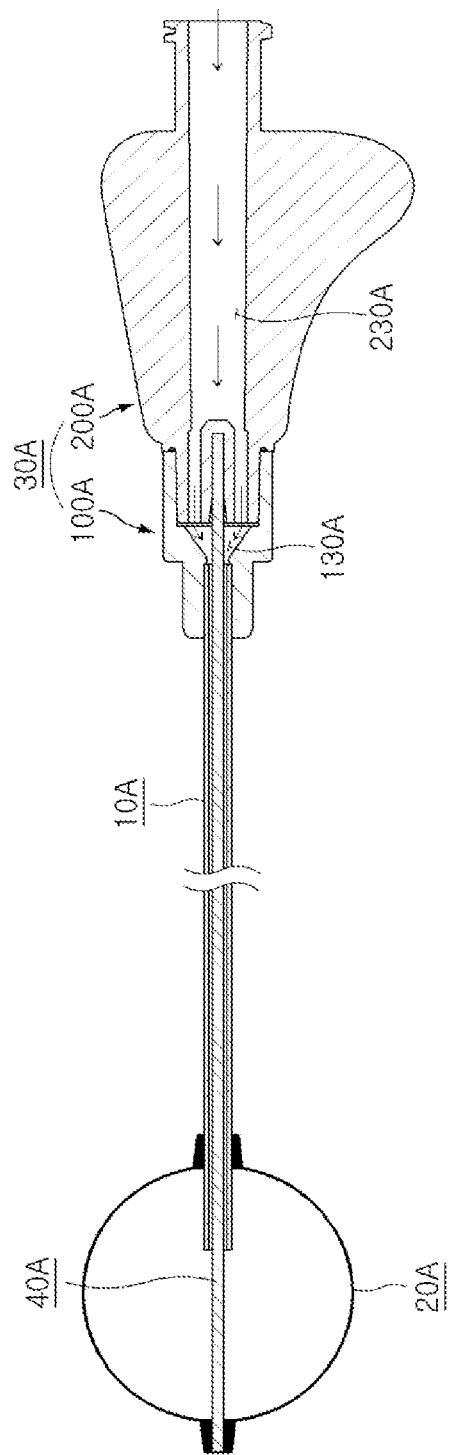

As illustrated in FIGS. 8 and 9, the balloon catheter according to the second embodiment of the present invention includes a catheter tube 10A having a proximal end portion 12A, a distal end portion 14A, and a lumen. The balloon catheter also includes a balloon 20A disposed on the distal end portion 14A of the catheter tube 10A, a connector 30A coupled to the proximal end portion 12A of the catheter tube 10A, and a guide wire 40A inserted into the catheter tube 10A to reinforce the strength of the catheter tube 10A.

The catheter tube 10A is elongated. The catheter tube 10A is formed as a tube, with opposite ends thereof being open, such that the proximal end portion 12A and the distal end portion 14A of the catheter tube 10A are open. The inner passage between the proximal end portion 12A and the distal end portion 14A of the catheter tube 10A forms the lumen.

The catheter tube 10A may be formed of a synthetic resin, such as polymer. The material of the catheter tube 10A is not limited thereto and may be modified variously. Thus, the catheter tube 10A may be formed of a material having a higher strength than a synthetic resin. For example, the catheter tube 10A may be formed of a metal, such as stainless steel or a shape memory alloy. The shape memory alloy may be implemented as nitinol, a nonmagnetic alloy of nickel (Ni) and titanium (Ti).

The guide wire 40A is formed longer than the catheter tube 10A. The guide wire 40A extends through the catheter tube 10A, such that opposite ends of the guide wire 40A (i.e. the proximal end portion 42A and the distal end portion 44A of the guide wire 40A) protrude (are exposed) externally from the catheter tube 10A through the openings of the proximal end portion 12A and the distal end portion 14A of the catheter tube 10A, and the portion of the guide wire 40A between the opposite ends 42A and 44A is disposed in the lumen.

A reinforcement member 46A is coupled to the distal end portion 44A of the guide wire 40A to increase the thickness of the distal end portion 44A of the guide wire 40A, thereby reinforcing the strength of the distal end portion 44A of the guide wire 40A. The reinforcement member 46A has a cap structure to be wrapped on the distal end portion 44A of the guide wire 40A. The reinforcement member 46A is formed of a synthetic resin, such as polymer, like the catheter tube 10A. However, the material of reinforcement member 46A is not limited thereto.

Figure 11:
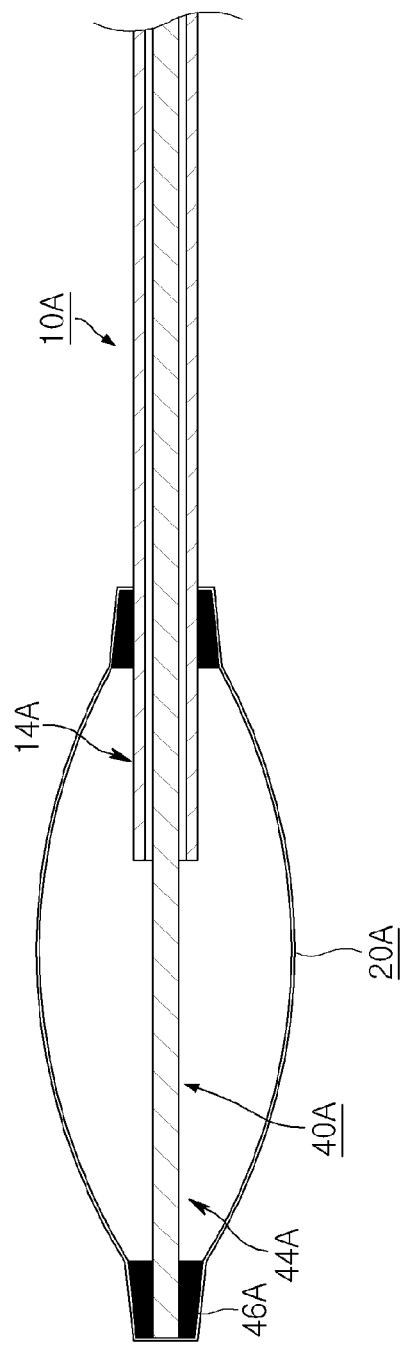
FIG. 11 is an enlarged view illustrating part B in FIG. 9.

Referring to FIGS. 9 and 11, the balloon 20A has two ends, one end being open and the other end being closed. The open end of the balloon 20A is fitted around and coupled to the outer circumference of the distal end portion 14A of the catheter tube 10A such that airtightness can be maintained, while the closed end of the balloon 20A is firmly coupled to the reinforcement member 46A while surrounding the reinforcement member 46A. The interior of the balloon 20A coupled as described above communicates with the lumen through the opening of the distal end portion 14A of the catheter tube 10A.

The balloon 20A as described above is formed of a synthetic resin that is extensible and compressible (shape recoverable). The balloon 20A may be formed of the same material as the catheter tube 10A and the reinforcement member 46A. The balloon 20A may be coupled to the outer circumference of the distal end portion 14A of the catheter tube 10A and the reinforcement member 46A by fusion. The balloon 20A may be coupled using an adhesive, a binding band, or the like depending on the material thereof.

Referring to FIGS. 9 and 12 to 14, the connector 30A has a fluid injection passage 130A and 230A through which fluid is injected from a fluid injector, such as a syringe. The fluid injection passage 130A and 230A extends through the connector 30A in the longitudinal direction. The connector 30A has a guide wire holder 240A and 250A supporting the proximal end portion 42A of the guide wire 40A to fix the guide wire 40A in position.

The connector 30A is formed of a synthetic resin, and includes first and second connector bodies 100A and 200A coupled to each other.

The first connector body 100A is coupled to the proximal end portion 12A of the catheter tube 10A. The first connector body 100A has a first engagement recess 110A on one end of both longitudinal ends, the proximal end portion 12A of the catheter tube 10A being fitted into the first engagement recess 110A, and a second engagement recess 120A on the other end of both longitudinal ends, the second engagement recess 120A allowing for fitting engagement with the second connector body 200A. The first passage 130A of the fluid injection passage 130A and 230A is formed between the first engagement recess 110A and the second engagement recess 120A. The interior of the first engagement recess 110A communicates with the interior of the second engagement recess 120A through the first passage 130A between the first engagement recess 110A and the second engagement recess 120A.

The inner circumference of the second engagement recess 120A is greater than that of the first engagement recess 110A. The first passage 130A is formed such that the size thereof increases gradually from the first engagement recess 110A to the second engagement recess 120A. A first projection may be formed between the first engagement recess 110A and the first passage 130A to limit a depth to which the proximal end portion 12A of the catheter tube 10A is inserted.

The coupled position between the first engagement recess 110A and the proximal end portion 12A of the catheter tube 10A may be maintained by an adhesive. In the catheter tube 10A and the first connector body 100A that are coupled to each other, the lumen and the first passage 130A communicate with other through the opening of the proximal end portion 12A of the catheter tube 10A.

The second connector body 200A has a fitting portion 210A on one of the longitudinal ends, the fitting portion 210A being fitted into the second engagement recess 120A, and a fluid injector engaging portion 220A on the other longitudinal end, the fluid injector engaging portion being coupled to the fluid injector engaging portion 220A. A second projection may be formed between the second engagement recess 120A and the first passage 130A to limit a depth to which the fitting portion 210A is inserted. The second connector body 200A has the second passage 230A extending between opposite ends in the longitudinal direction to pass through the second connector body 200A. The opening of the proximal end portion of the second passage 230A is positioned on the fluid injector engaging portion 220A, and the opening of the distal end portion of the second passage 230A is positioned on the fitting portion 210A.

The coupled position of the second engagement recess 120A and the fitting portion 210A may be maintained using an adhesive. In the second engagement recess 120A and the fitting portion 210A coupled to each other, the first passage 130A and the second passage 230A communicate with each other. The second passage 230A communicating with the first passage 130A forms the fluid injection passage 130A and 230A together with the first passage 130A.

The proximal end portion 42A of the guide wire 40A is positioned on the distal end portion of the second passage 230A beyond the first passage 130A, and the guide wire holder 240A and 250A is positioned on the distal end portion of the second passage 230A.

Figure 12:
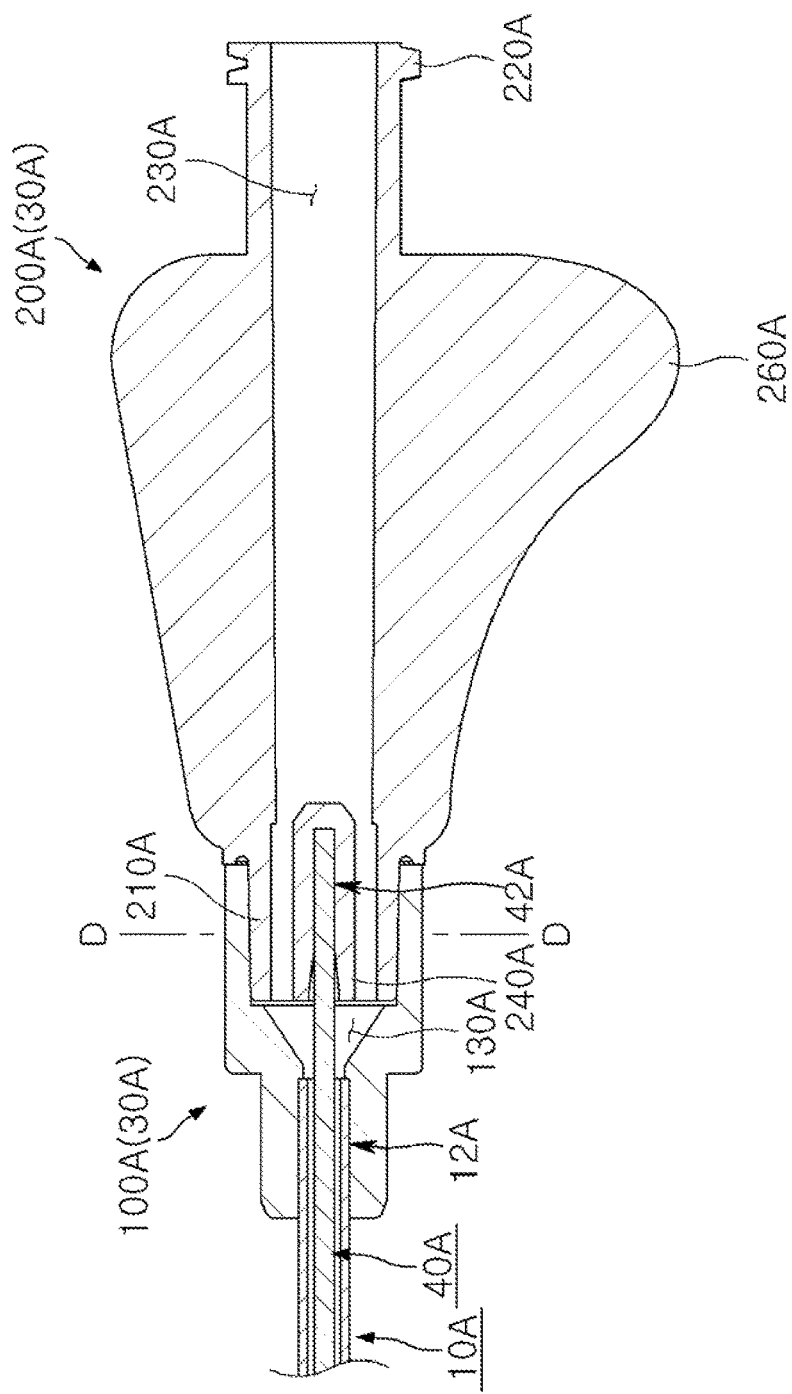
FIG. 12 is an enlarged view illustrating part C in FIG. 9.
Figure 13:
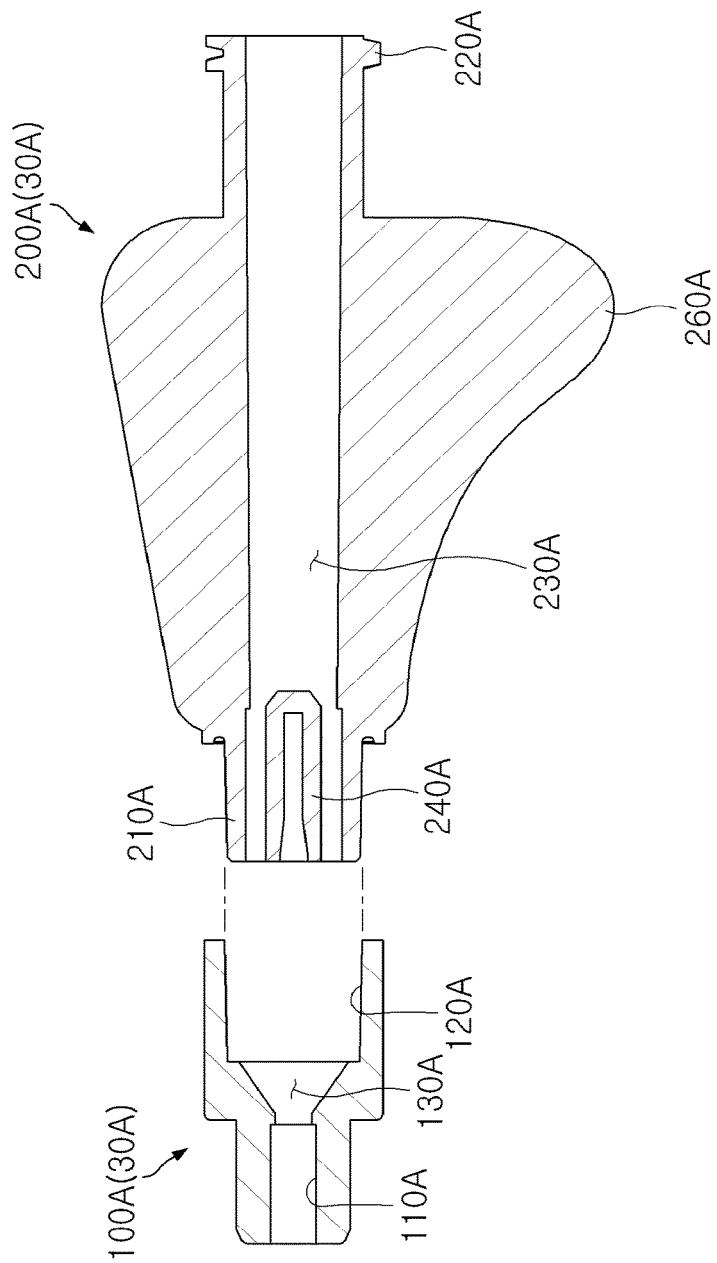
FIG. 13 illustrates a separated position of the connector illustrated in FIG. 12.
Figure 14:
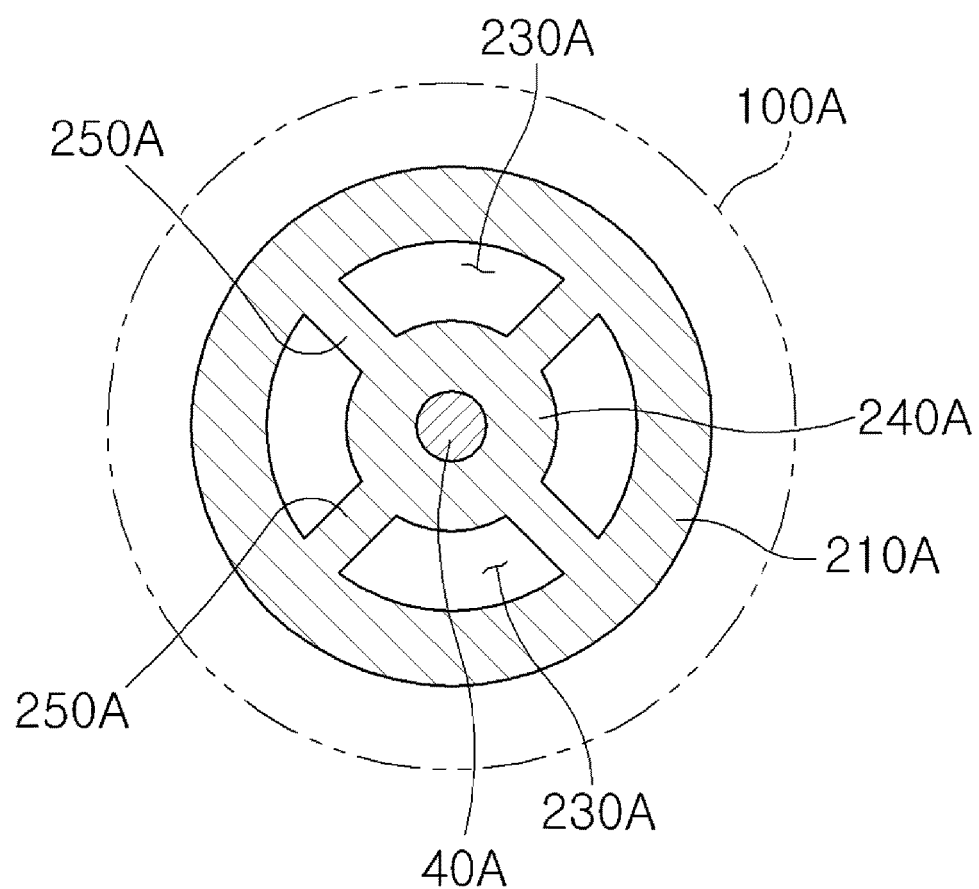
FIG. 14 is a cross-sectional view taken along line D-D in FIG. 12

As illustrated in FIGS. 12 to 14, the guide wire holder 240A and 250A includes a holder body 240A disposed on the central portion of the cross-section of the second passage 230A and one or more support arms 250A supporting the holder body 240A on the inner wall of the second passage 230A.

The holder body 240A supports the proximal end portion 42A of the guide wire 40A. The holder body 240A is configured to have a cup structure, such that the proximal end portion 42A of the guide wire 40A can be fitted into the holder body 240A. It is preferable that a plurality of support arms 250A are provided. The plurality of support arms 250A may be arranged radially around the holder body 240A and may be spaced apart from each other.

Reference numeral 260A indicates a knob. One or more knobs 260A are provided on the outer circumference of the second connector body 200A.

The balloon catheter according to the second embodiment of the present invention is inserted into an intended position within the body from the skin of the subject, with the balloon 20A being contracted. In this process, the operator can easily insert the balloon catheter according to the present invention due to the reinforcement member 46A reinforcing the strength of the distal end portion 44A of the guide wire 40A. In addition, the reinforcement member 46A can prevent the balloon 20A from being damaged (torn) by the distal end portion 44A of the guide wire 40A.

In the position in which the balloon catheter according to the second embodiment of the present invention is inserted into the body, when fluid (possibly liquid) is injected using the fluid injector, fluid flows sequentially through the second passage 230A, the first passage 130A, and the lumen of the catheter tube 10A and then is discharged through the opening of the distal end portion 14A of the catheter tube 10A to enter the balloon 20A. Then, the balloon 20A is inflated to expand or restore the corresponding tissues.

In the balloon catheter according to the second embodiment of the present invention as described above, the single lumen acts as the guide wire lumen, through which the guide wire 40A is inserted, and the inflating lumen, through which fluid is delivered. It is thereby possible to simply fabricate the balloon catheter, reduce inconvenience to the operator, and form the catheter tube 10A to be more slender.

Although the present invention has been described for illustrative purposes, the present invention is by no means limited to the embodiments disclosed herein and the accompanying drawings. It should be understood that various modifications are possible to a person skilled in the art without departing from the scope and spirit of the present invention as disclosed in the accompanying claims.

For example, although the balloon catheter according to the first embodiment of the present invention has been illustrated as including the resilient member 50 formed of a mesh as the extension/compression restricting means, an elastic member, such as a coil spring, may be applied as the resilient member 50.

What is claimed is:
1. A balloon catheter comprising:
a catheter tube comprising a proximal end portion, a distal end portion, and a single lumen extending between the proximal end portion and the distal end portion in a longitudinal direction;
a guide wire inserted in the lumen of the catheter tube and extending through the catheter tube, the guide wire having a cross section smaller than a diameter of the lumen to define a fluid passage way in the lumen around the guide wire;
a connector comprising a first connector body coupled to the proximal end portion of the catheter tube, and the first connector body having a first passage communicating with the lumen, and a second connector body coupled to the first connector body, the second connector body having a second passage serially communicating with the first passage to form a fluid injection passage together with the first passage to supply fluid to the lumen; and
a balloon disposed on the distal end portion of the catheter tube and configured to be inflated by the fluid supplied to the lumen via the fluid injection passage,
wherein the connector further comprises a guide wire holder received in the second passage of the second connector body, the guide wire holder comprising a holder body supporting a proximal end portion of the guide wire in a central portion of the fluid injection passage, and a plurality of support arms disposed around the holder body and spaced apart from each other to support the holder body on an inner wall of the fluid injection passage while defining fluid flow conduits between the spaced support arms, the fluid flow conduits communicating with the first passage of the first connector body and the second passage of the second connector body to enable fluid supply to the lumen through the fluid flow conduits.

2. The balloon catheter according to claim 1, wherein the guide wire passes through the catheter tube, such that a distal end portion of the guide wire protrudes from the catheter tube, and a reinforcement member is coupled to the distal end portion of the guide wire.

3. The balloon catheter according to claim 2, wherein the balloon is coupled to the catheter tube and the reinforcement member, with a proximal end of the balloon being fitted around an outer circumference of the distal end portion of the catheter tube, and a distal end of the balloon surrounding the reinforcing member.

4. The balloon catheter according to claim 1, wherein the connector comprises a knob at an outer surface thereof.

5. The balloon catheter according to claim 1, wherein the first connector body comprises:
a first engagement recess on a distal end, into which the proximal end portion of the catheter tube is fitted; and
a second engagement recess on a proximal end, allowing for fitting engagement with the second connector body, wherein the first passage of the first connector body extends in the longitudinal direction between the first engagement recess and the second engagement recess, and wherein the second connector body comprises a fitting portion fitted into the second engagement recess.

* * * * *